US00PP19579P3

(12) United States Plant Patent
Hemstad et al.

(10) Patent No.: US PP19,579 P3
(45) Date of Patent: Dec. 16, 2008

(54) GRAPEVINE PLANT NAMED 'MARQUETTE'

(50) Latin Name: *Vitis spp*
Varietal Denomination: Marquette

(75) Inventors: Peter Hemstad, Edina, MN (US); James Luby, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 110 days.

(21) Appl. No.: 11/580,356

(22) Filed: Oct. 13, 2006

(65) Prior Publication Data

US 2007/0089208 P1 Apr. 19, 2007

Related U.S. Application Data

(60) Provisional application No. 60/726,264, filed on Oct. 13, 2005.

(51) Int. Cl.
*A01H 5/00* (2006.01)

(52) U.S. Cl. ..... Plt./205
(58) Field of Classification Search ..... Plt./205
See application file for complete search history.

*Primary Examiner*—Kent L Bell
(74) *Attorney, Agent, or Firm*—Penny J. Aguirre

(57) ABSTRACT

The invention is a new and distinct variety of grape vine plant designated 'Marquette', which produces bluish-black colored fruit suitable for red wine production, and has a combination of high wine quality, excellent cold hardiness and good disease resistance.

4 Drawing Sheets

Botanical classification: *Vitis* spp hybrid.
Variety denomination: 'Marquette'.

BACKGROUND OF THE INVENTION

The present invention relates to a new and distinct cultivar of grape plant botanically known as *Vitis* spp. hybrid 'Marquette', referred to hereafter by its cultivar name, 'Marquette'.

'Marquette' is a grape with dark blue fruit that has been shown to be very cold hardy, disease resistant, and reasonably productive for 10 years in east central Minnesota. It has also been tested in a number of other states. The fruit of 'Marquette' can be used to make a high quality red table wine.

'Marquette' was discovered in 1997 in vineyard Block 1 Row 20 at the University of Minnesota's Horticultural Research Center near Excelsior, Minn. 'Marquette' originated from a cross made in 1989 between 'MN 1094' (not patented) and the French Hybrid cultivar 'Ravat 262' (not patented). 'MN 1094' was derived from a complex parentage including *V riparia, V. vinifera,* and lesser amounts of several other *Vitis* species. 'Ravat 262' likewise has a complex background, including several *Vitis* species and the renowned variety *V. vinifera,* 'Pinot noir' (not patented) as one of its parents.

Asexual reproduction of the new cultivar was first accomplished by means of rooting of hardwood cuttings by the inventors at the University of Minnesota's Horticultural Research Center near Excelsior, Minn. The asexual progeny of 'Marquette' propagated in this manner have been determined to be stable and true to type in successive generations.

SUMMARY OF THE INVENTION

The following traits have been repeatedly observed and represent the characteristics of the new cultivar. 'Marquette' has not been observed under all possible environmental conditions. The phenotype may vary somewhat with variations in temperature, day length, light intensity, soil types and water and fertility levels, without, however, any variance in the genotype. The measurements, observations and descriptions that follow describe plants grown outdoors and observed for six years in Excelsior, Minn.

'Marquette' plants have been cold hardy in east central Minnesota, having withstood temperatures as low as −36° F. without serious injury. In this part of Minnesota the plants are routinely exposed to midwinter temperatures near −20° F. and exhibit no injury. Based on its winter hardiness, 'Marquette' should be a useful grape for wine production not only in the upper Midwest U.S. but also in the Great Lakes and New England regions.

The plants of 'Marquette' exhibit an open and orderly growth habit that is highly desirable for efficient vineyard management and fruit exposure to the sun, which is conducive to maximizing wine quality.

Resistance to common grape diseases including downy mildew (Plasmopara viticola), powdery mildew (Uncinula necator), and black rot (Guignardia bidwellii), has been very good. The plants can be grown with only minimal fungicide sprays in east central Minnesota.

Resistance to foliar infestation by the insect pest phylloxera (Daktulosphaira vitifoliae) has been moderate, but 'Marquette' plants exhibit less infestation than 'Frontenac' (not patented), the main red wine grape variety in Minnesota.

'Marquette' typically has no more than two small to medium clusters per shoot, thus avoiding the need to remove clusters (cluster thinning) to reduce crop level in order to maintain high fruit quality. Fruit yield from 'Marquette' plants in experimental plots have averaged 5.46 Kg/vine or the equivalent of 3.6 tons/acre.

'Marquette' fruit ripens in mid-season, a few days before the standard cultivar 'Frontenac'. Sugar levels in the fruit have been high, averaging 26.1° brix. Acid levels have also been higher than most cultivars (1.21%) although substantially lower than that of 'Frontenac' (1.50%). This level of titratable acidity has been found to be quite manageable by use of standard winemaking procedures such as malolactic fermentation and chemical acid reduction.

Experimental wines made from 'Marquette' fruit have been excellent, exceeding nearly all non-*V. vinifera* varieties in quality ratings. Tasters have noted an attractive deep red color, desirable aromas of cherry, black pepper, spice, and berry, and substantial tannin structure rarely found in wines not produced from varieties of *V. vinifera*.

'Marquette' is distinguished from its parent 'MN 1094' by its much lower vigor level and its lack of red color (anthocyanin) in its leaves in the fall.

'Marquette' is distinguished from its parent 'Pavat 262' by its much smaller berry size (1.14 vs. 1.83 g) and the rectilinear teeth of most of its leaves, as opposed to the convex teeth of 'Ravat 262'.

The main feature distinguishing 'Marquette' from other grape varieties that are commonly grown for red wine production in areas with winter minimum temperatures of −20° F. such as 'Frontenac', 'St. Croix' (U.S. Plant Pat. No. 4,928) and 'Marechal Foch' (not patented) is the presence of substantial amounts of tannins in the wine which, along with fruity and spicy flavors, give it greater complexity in flavor than wines from the other varieties.

BRIEF DESCRIPTION OF THE FIGURES

The accompanying color photographs represent typical mature berry clusters and vines of 'Marquette' as grown under standard field conditions in Excelsior, Minn.

The photograph in FIG. 1 is a close-up view of clusters of berries of 'Marquette' in mid September.

Figure 1:
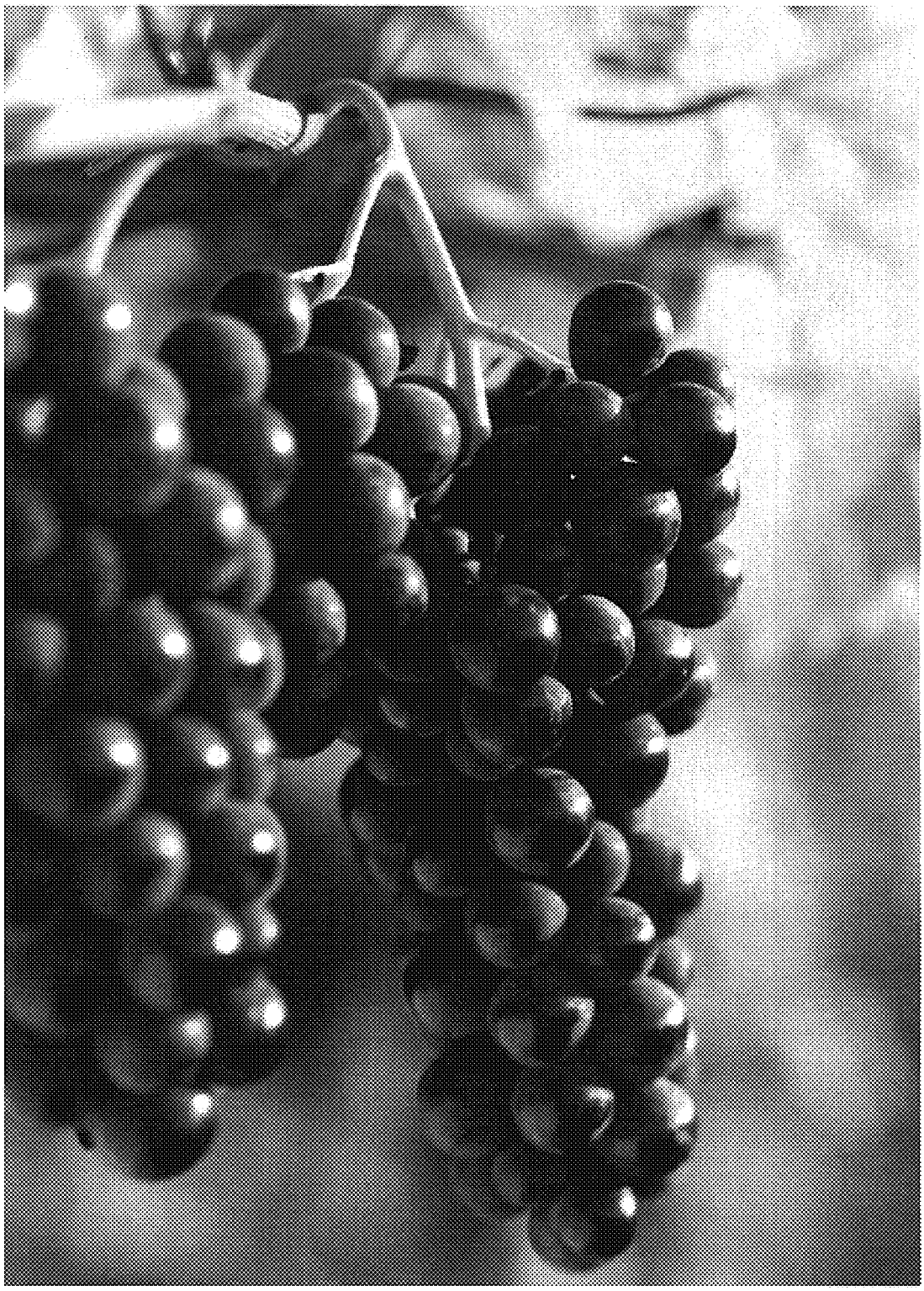
Figure 2:
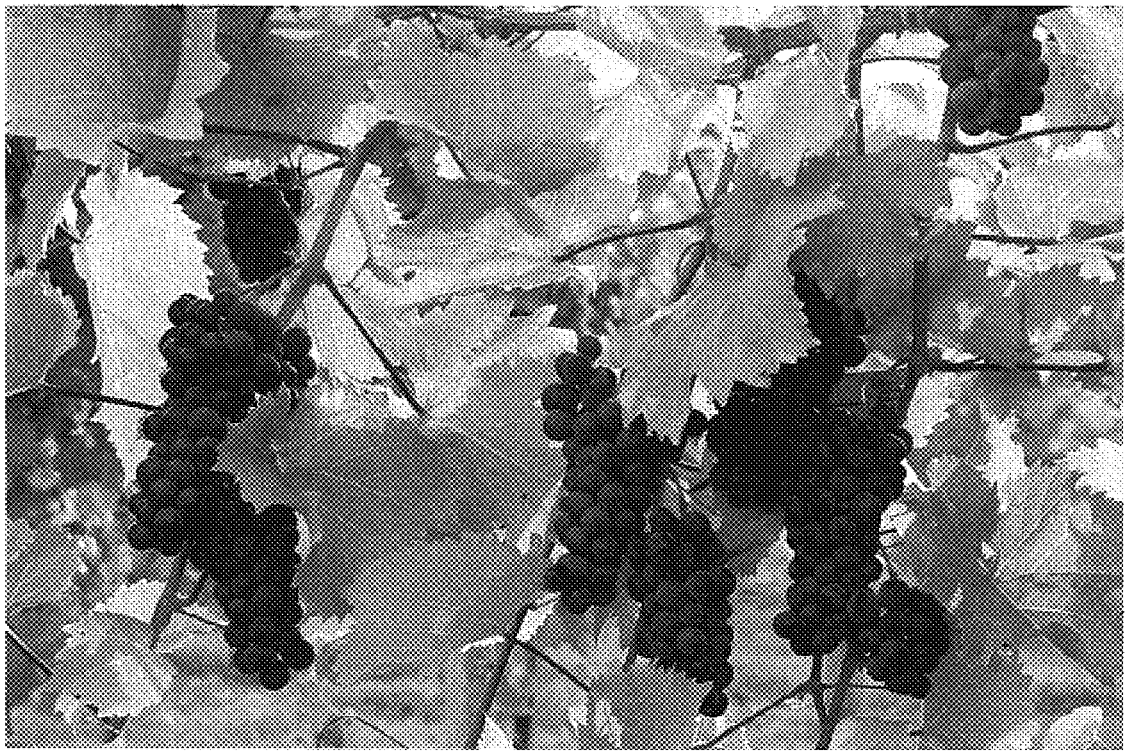

The photograph in FIG. 2 shows clusters and leaves of 'Marquette' in mid September.

Figure 3:
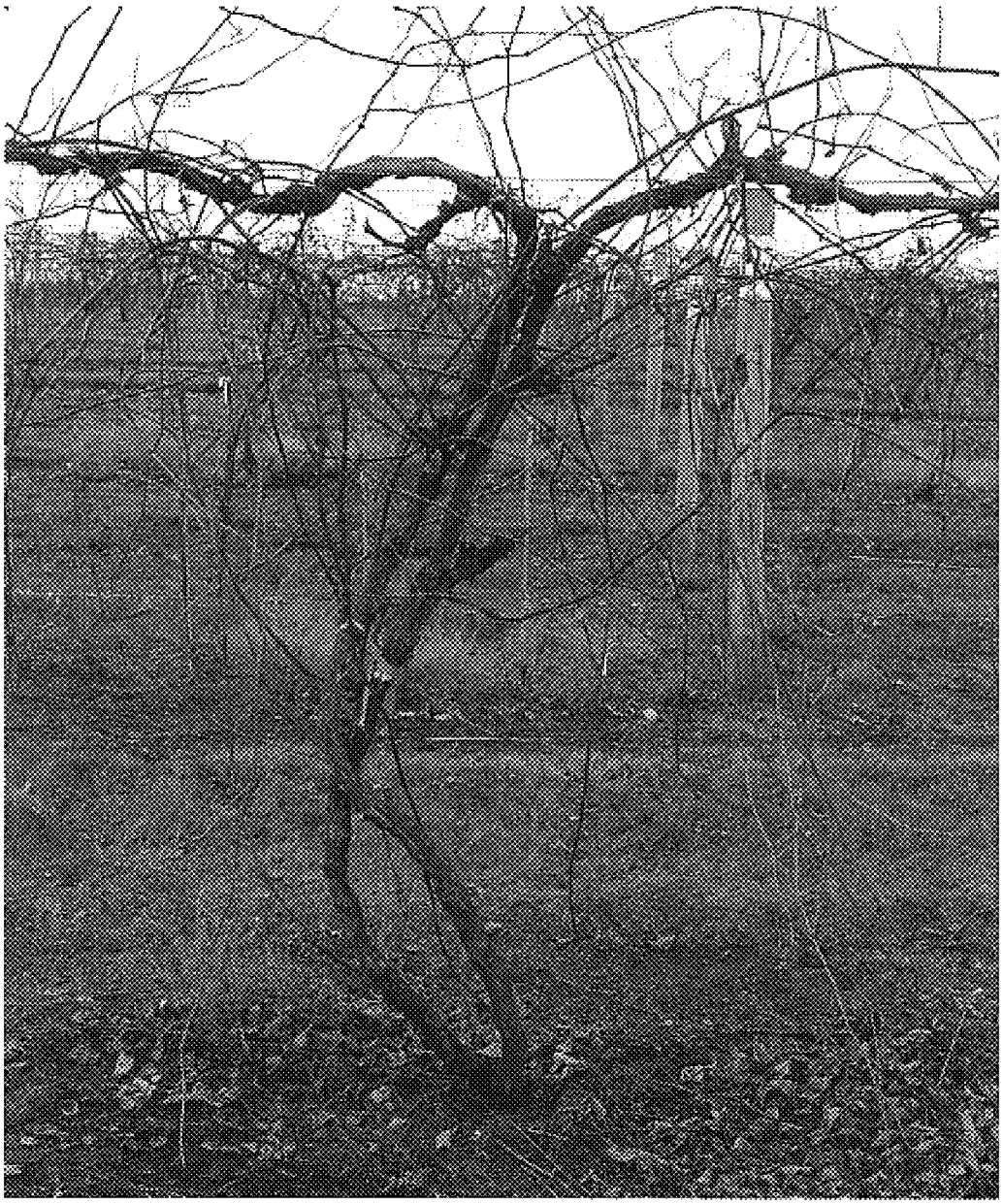

FIG. 3 shows a mature vine of 'Marquette' in mid November.

Figure 4:
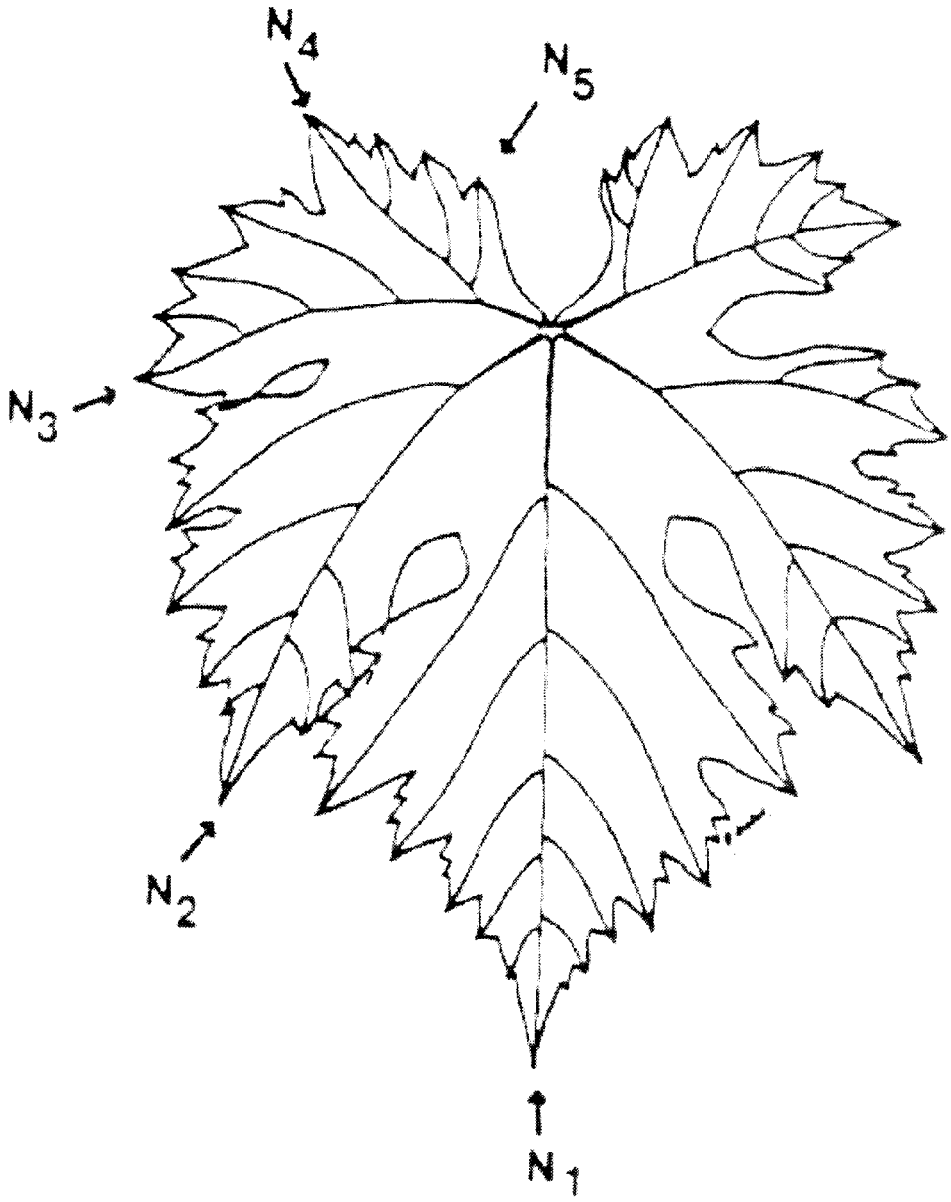

FIG. 4 is a drawing taken from Dettweiler E., 1991, 'Preliminary Minimal Descriptor List for Grapevine Varieties', Institüt fur Rebenzüchtung, Geilweilerhof, Germany: N1 is the length along the primary vein (midrib) from the tip of the blade to the petiole sinus, N2 is the length of the vein from the tip of the first major lobe of the blade to the petiole sinus, N3 is the length of the vein from the tip of the second major lobe of the blade to the petiole sinus, N4 is the length of the vein from the tip of the third major lobe of the blade to where it joins the vein measured in N3, N5 is the length of the vein from the tip of the first tooth proximal to the petiole sinus to where it joins the vein measured in N4.

The colors in the photographs are as close as possible with the photographic and printing technology utilized. The color values cited in the detailed botanical description accurately describe the colors of the new grape.

DETAILED BOTANICAL DESCRIPTION

The following data pertain to vines grown in Carver County, Minn. near Excelsior. Alphanumeric color designations refer to values based on the 1995 R.H.S. Colour Chart published by The Royal Horticultural Society, London, England. Many of the descriptors are based on those set forth by the International Board for Plant Genetic Resources in collaboration with the Office Internationale de la Vigne et du Vin (OIV) and the International Union for the Protection of New Varieties of Plants. When dimensions, sizes, colors and other characteristics are given, it is to be understood that such characteristics are approximations set forth as accurately as possible. Variations of the usual magnitude incident to climatic factors, fertilization, pruning, pest control and other cultural practices are to be expected.

Botanical classification: Cultivar of *Vitis* with ancestry tracing to several species including *V. vinifera* and *V. riparia*.

Parentage: 'MN 1094' (female), 'Ravat 262' (male).

*A*) *Mature canes.*—The values presented are the means (with ranges in parentheses) of 10 canes observed from the 2004 and 2007 growing seasons. 1. Color of canes: striated, reddish brown RHS colors 165A and 165B 2. Length of canes: 1.46 m (0.88–2.12) 3. Diameter of canes: 6.1 mm (4.2–9.1) 4. Internode length at base: 1.3 cm (0.8–1.5) 5. Internode length at midpoint: 7.8 cm (5.5–11.2) 6. Lenticels present: yes (very small) 7. Lenticel color 200A 8. Cane cross-section shape: elliptical 9. Density of hairs on mature cane: none 10. Tendril pattern on shoot: 2,0, 2,0 etc. (two nodes with a tendril followed by one node without) 11. Tendrils forked: yes 12. Tendril texture: striated 13. Tendril length: 16.5 cm (9.3–23.0) 14. Tendril color: 166C 15. Bud width: 3.0 mm (2.0–3.2) 16. Bud length: 5.2 mm (4.1–7.0) 17. Bud shape: triangular 18. Bud color: 165A.

*B*) *Trunk.*—The observations presented are from the 2005 growing season. 1. Bark texture: somewhat flaky, small vertical segments approximately 0.45 cm×5.0 cm 2. Bark color: striated, 201C and 201D.

*C*) *Mature leaves.*—Ten representative mature leaves from above the clusters in the middle third of the shoot were examined. The leaves were pressed and dried for later analysis. The values presented below are means (with ranges in parentheses) from collections in 2004. Descriptors of mature leaves, including the designations N1 through N5, relate to "OIV-Code Numbers 065–093" of Preliminary Minimal Descriptor List for Grapevine Varieties (Dettweiler E., 1991, Institüt fur Rebenzüchtung, Geilweilerhof, Germany). 1. Length of blade: 13.1 cm (11.7–14.7) 2. Width of blade: 11.6 cm (10.9–13.0) 3. Shape of blade: wedge-shaped 4. Number of lobes: 0 5. Length of vein N1: 9.8 cm (8.9–11.0) 6. Length of vein N2: 7.9 cm (7.3–9.2) 7. Length of vein N3: 5.5 cm (4.8–6.2) 8. Length of vein N5: 1.6 cm (0.7–1.9) 9. Length of N2 teeth: 1.3 cm (0.7–1.6) 10. Width of N2 teeth: 1.2 cm (0.8–1.5) 11. Length/width ratio of N2 teeth: 1.14 (0.88–1.22) 12. Length of N4 teeth: 6.7 mm (5–9) 13. Width of N4 teeth: 8.6 mm (7–10) 14. Length/width ratio of N4 teeth: 0.78 (0.71–0.90) 15. Shape of teeth: mostly rectilinear with some convex on both sides 16. Shape of petiolar sinus: wide open 17. Shape of base of petiolar sinus: v-shaped 18. Depth of petiolar sinus: 2.4 cm (1.7–2.7) 19. Width of petiolar sinus: 2.3 cm (1.4–4.4) 20. Length of petioles: 6.0 cm (3.3–7.4) 21. Shape of upper sinuses: none 22. Shape of base of upper sinuses: none 23. Pubescence on adaxial surface: none 24. Pubescence on abaxial surface: very small erect hairs on veins 25. Color of adaxial leaf surface: 146A yellow-green 26. Color of abaxial leaf surface: 146B yellow-green 27. Color of leaf petiole 183A, 59A.

*D*) *Young shoots.*—The observations presented are from the 2005 growing season. 1. Form of shoot tip: half open 2. Density of prostate hairs on tip: none 3. Density of erect hairs on tip: moderate 4. Petiole pigmentation: 59A reddish purple on adaxial, 144B yellow-green on abaxial 5. Shoot pigmentation: 144B yellow green in color and striped 59A reddish purple on adaxial.

*E*) *Flowers.*— 1. Fragrance: moderately fragrant 2. Mean time of flowering: June 15 when grown in Excelsior, Minn. 3. Color of petal: 145A, yellow-green on both surfaces 4. Color of sepal: 144A, yellow-green on abaxial, adaxail not visible 5. Sepal number: sepals fused into continuous calyx 6. Calyx shape: ring-shaped 7. Calyx length: 0.5 mm (0.4–0.6) 8. Calyx width: 1.5 mm (1.4–1.7) 9. Calyx apex: fused to ovary 10. Calyx base: fused to pedicel 11. Calyx surface: glabrous 12. Color of pollen: 4B, yellow 13. Petal number: 5, fused in calyptra 14. Petal shape: cohering at summit and separating at base: 2.5 mm long; 1 mm wide at fused end; reflexed after dehiscence 15. Shape of cluster: slightly conical, sometimes with one shoulder 16. Size of cluster: 8.8 cm long (6.9–11.1); 4.5 cm wide (3.7–7.2) 17. Number of flowers per cluster: 118 (92–147) 18. Size of individual entire flower: 6.3 mm in height, 4.0 mm wide 19. Pollen fertility: yes, based on use in controlled crosses 20. Color of stamen: Anther: 162C, grayed yellow Filament: 155A, white 21. Stamen number: 5.0 (4–6) 22. Pistil number: 1 per flower 23. Pistil length: 2.4 mm 24. Color of pistil: 144A, yellow-green.

*F*) *Fruit.*—The values presented below are means (with ranges in parentheses) from fruit observed in the 2004 growing season, except for those traits indicated (), which are means from the 2001–2004 growing seasons. 1. Cluster length: 10.6 cm (8.5–13.4) 2. Cluster diameter: 6.1 cm (4.9–7.7) 3. Cluster weight: 85.3 g (65.4–124.8) 4. Cluster density: medium, average of 74.5 berries per cluster 5. Berry weight:** 1.14 g (0.89–1.31) 6. Berry length: 12.8 mm (11–14) 7. Berry diameter at equator: 11.9 mm (10–13) 8. Berry shape: roundish 9. Berry cross-section: circular 10. Berry, color of skin: 202A black with 98D bluish bloom 11. Berry, color of flesh: 63C light pink 12. Berry, particular flavor: neutral 13. Length of pedicel: 5.0 mm (3.3–6.9) 14. Pedicel diameter: 1.2 mm (0.9–1.4) 15. Pedicel color 144B yellow-green 16. Berry, separation from pedicel: difficult 17. Berry, presence of seeds: fully developed 18. Seed number/berry: 2.1 (1–4) 19. Seed length: 0.61 mm (0.51–0.78) 20. Seed width: 0.41 mm (0.32–0.5) 21. Seed length/width ratio: 1.49 22. Seed weight: 0.024 g 23. Seed color: 200C.

*G*) *Harvest parameters.*—Values represent the means (with ranges in parentheses) for fruit harvested over five growing seasons 2000–2004). 1. Harvest date: 9/21 (9/10–10/6) 2. Brix: 26.1° (25.0°–28.6°) 3. pH: 2.95 (2.86–3.12) 4. % titratable acidity: 1.21% (1.02%–1.37%).

*H*) *Vineyard performance.*—Based on observations compiled over four years (2002–2005) 1. Susceptibility to powdery mildew (Uncinula necator): low 2. Susceptibility to downy mildew (Plasmopara vilicola): low 3. Susceptibility to black rot (Guignardia bidwellii): low 4. Susceptibility to bunch rot (Botrytis, etc): low 5. Susceptibility to foliar phylloxera (Daktulosphaira vitifoliae): moderate 6. Susceptibility to crown gall (Agrobacterium tumefaciens): none observed 7. Susceptibility to phenoxy herbicide drift (e.g., 2,4-D): low 8. Berry splitting: low 9. Berry shelling: very low 10. Vigor level: moderate 11. Winter hardiness: high, trunks have survived −38° C. 12. Wood ripening: very good.

*I*) *Wine quality.*—Descriptions below are compiled from observations on wine made from 'Marquette' fruit harvested during the 2000–2004 seasons. 1. Flavors and aromas: cherry, spice, black pepper, berry 2. Balance: well balanced, good body and tannin structure 3. Color: attractive deep red 4. Propensity for oxidation: low 5. Overall quality: very good.

We claim:

1. A new and distinct variety of grapevine plant designated 'Marquette' as described and illustrated herein.

* * * * *